(12) United States Patent
Kremeier (10) Patent No.: US 12,274,827 B2
(45) Date of Patent: Apr. 15, 2025

(54) METHOD AND APPARATUS FOR DETERMINING A REGIONAL COMPLIANCE OF A LUNG DURING SPONTANEOUS RESPIRATION

(71) Applicant: Loewenstein Medical Technology S.A., Luxembourg (LU)

(72) Inventor: Peter Kremeier, Karlsruhe (DE)

(73) Assignee: LOEWENSTEIN MEDICAL TECHNOLOGY S.A, Luxembourg (LU)

( * ) Notice: Subject to any disclaimer, the term of this patent is extended or adjusted under 35 U.S.C. 154(b) by 1107 days.

(21) Appl. No.: 17/168,268

(22) Filed: Feb. 5, 2021

(65) Prior Publication Data
US 2021/0244901 A1    Aug. 12, 2021

(30) Foreign Application Priority Data
Feb. 7, 2020 (DE) .......................... 102020103145.9

(51) Int. Cl.
| | |
|---|---|
| A61M 16/00 | (2006.01) |
| A61B 5/0536 | (2021.01) |
| A61B 5/085 | (2006.01) |

(52) U.S. Cl.
CPC ......... *A61M 16/024* (2017.08); *A61B 5/0536* (2013.01); *A61B 5/085* (2013.01);
(Continued)

(58) Field of Classification Search
CPC ............ A61M 16/024; A61M 16/0057; A61M 2205/502; A61M 2230/65; A61B 5/0536; A61B 5/085
See application file for complete search history.

(56) References Cited

U.S. PATENT DOCUMENTS

| | | |
|---|---|---|
| 9,987,446 B2 | 6/2018 | Novotni et al. |
| 2003/0216664 A1* | 11/2003 | Suarez ................. A61B 5/0536 600/547 |

(Continued)

FOREIGN PATENT DOCUMENTS

DE    102013203177 A1    8/2014

OTHER PUBLICATIONS

Tobias H Becher et al: "Assessment of respiratory system compliance with electrical impedance tomography using a positive end-expiratory pressure wave maneuver during pressure support ventilation: a pilot clinical study", Critical Care, Biomed Central Ltd London, GB, vol. 18, No. 6, Dec. 10, 2014 (Year: 2014).*

*Primary Examiner* — Valerie L Woodward
(74) *Attorney, Agent, or Firm* — Abel Schillinger, LLP (57) ABSTRACT

A method for determining a regional compliance of a lung during spontaneous respiration. In the method, a lung compliance value C.M is determined by triggering an inspiration maneuver and either measuring a compliance of the entire lung or of a surrogate for the compliance of the entire lung. In the method, there further is a capture of an electrical impedance distribution along at least one two-dimensional section through a human thorax by a device for electrical impedance tomography, with a multiplicity of EIT pixels being captured. An end-inspiratory and an end-expiratory electrical impedance are determined for each EIT pixel and an impedance difference is determined for each EIT pixel. The regional compliance is determined for specific EIT pixels, which are assigned to an impedance value range based on a frequency distribution of all EIT pixels.

20 Claims, 1 Drawing Sheet

(52) U.S. Cl.
CPC ... *A61M 16/0057* (2013.01); *A61M 2205/502* (2013.01); *A61M 2230/65* (2013.01)

(56) References Cited

U.S. PATENT DOCUMENTS

| | | | |
|---|---|---|---|
| 2009/0114222 A1* | 5/2009 | Ralfs | A61M 16/0051 128/204.23 |
| 2013/0002264 A1* | 1/2013 | Garber | A61B 5/08 324/600 |
| 2015/0287186 A1* | 10/2015 | Holzhacker | A61B 5/08 382/131 |
| 2016/0008561 A1* | 1/2016 | Novotni | A61B 5/0536 128/204.23 |
| 2018/0078168 A1* | 3/2018 | Gärber | A61M 16/024 |
| 2019/0038173 A1* | 2/2019 | Gärber | A61B 5/0871 |

* cited by examiner

METHOD AND APPARATUS FOR DETERMINING A REGIONAL COMPLIANCE OF A LUNG DURING SPONTANEOUS RESPIRATION

CROSS-REFERENCE TO RELATED APPLICATIONS

The present application claims priority under 35 U.S.C. § 119 of German Patent Application No. 102020103145.9, filed Feb. 7, 2020, the entire disclosure of which is expressly incorporated by reference herein.

BACKGROUND OF THE INVENTION

1. Field of the Invention

The invention relates to a method for determining a regional compliance of a lung during spontaneous respiration. The invention further relates to a system for determining a regional compliance of a lung during spontaneous respiration. Moreover, the invention relates to a ventilator comprising the system for determining the regional compliance.

2. Discussion of Background Information

In physiology, the term compliance is understood to mean the flexibility of respiratory and vessel systems. A state of lung tissue can be assessed on the basis of the compliance of the lung. To ascertain the compliance of the lung, an increase in volume of the lung is related to a filling pressure. The higher the compliance, the greater the extension of the lung tissue when a certain filling pressure is applied to the lung. By contrast, lung tissue with a low compliance is comparatively stiff. A low compliance of the lung can be due to various diseases. By way of example, parameters of ventilators can be set on the basis of the compliance in order to facilitate operation that spares the lungs to the greatest possible extent during artificial ventilation by means of the ventilator. The compliance of a lung can be measured comparatively easily under mandatory ventilation. By contrast, this is not the case during spontaneous respiration on account of the elastic restoration forces of the lung and the diaphragm activity.

Spatially differentiated information items in respect of the state of a lung can be obtained by means of EIT (electrical impedance tomography). EIT is a non-invasive method in which electrical conductivity is measured on the human body. EIT pixels are recorded in the process, each EIT pixel representing an electrical conductivity of the human body in a certain body area. If this method is carried out in the region of the lung, different values arise for the EIT pixels depending on the state of the lung. Differences in the electrical conductivity arise, in particular, on the basis of the aeration of the lung. As a result, it is possible to draw conclusions about the state of the alveoli in certain regions of the lung, for example. EIT can be carried out directly at the bed of the patient. For details about EIT, reference is made to document DE 10 2013 203177 A1, the entire disclosure of which is incorporated by reference herein.

The term regional compliance describes the compliance in certain regions of the lung. The regional compliance provides clinically relevant information items for estimating the inhomogeneity of the lung. It can also be helpful when estimating effects on changes in ventilation parameters and when carrying out ventilation maneuvers.

In view of the foregoing, it would be advantageous to have available a method for determining a regional compliance of a lung, for example during spontaneous respiration. It further would be advantageous to have available a system for determining a regional compliance of a lung, for example during spontaneous respiration, as well as a ventilator which allows a regional compliance of a lung to be ascertained, for example during spontaneous respiration.

SUMMARY OF THE INVENTION

The present invention provides a method for determining a regional compliance of a lung, for example during spontaneous respiration, a system for determining a regional compliance of a lung during spontaneous respiration, a ventilator, and a device for electrical impedance tomography as set forth in the instant independent claims.

The dependent claims relate to various mutually independent, advantageous developments of the present invention, the features of which, within the scope of what is technically feasible, can be combined freely with one another by a person skilled in the art. In particular, this also applies beyond the boundaries of the various claim categories.

According to a first aspect of the invention, a method for determining a regional compliance $C.REG_i$ of a lung during spontaneous respiration is proposed. In the method, a lung compliance value C.M is determined by triggering an inspiration maneuver and either measuring the compliance of the entire lung or measuring a surrogate for the compliance of the entire lung. In the method, there further is a capture of an electrical impedance distribution along at least one two-dimensional section through a human thorax by means of a device for electrical impedance tomography. In the method, there further is a division of the captured electrical impedance distribution at different times into a multiplicity of EIT pixels. In the method, there further is a determination of an end-expiratory electrical impedance Z.EXSP for each EIT pixel and an end-inspiratory electrical impedance Z.INSP for each EIT pixel. In the method, there further is a determination of an impedance difference $\Delta Z$ for each EIT pixel by virtue of calculating a difference between the end-inspiratory electrical impedance Z.INSP and the end-expiratory electrical impedance Z.EXSP. Preferably, the end-expiratory electrical impedance Z.EXSP is subtracted from the end-inspiratory electrical impedance Z.INSP to this end. In the method, there further is a provision of a plurality of impedance value ranges and an assignment of the EIT pixels to the impedance value ranges on the basis of the respective impedance difference $\Delta Z$ of the EIT pixels. In the method, there further is a determination of the regional compliance $C.REG_i$ for specific EIT pixels, which are assigned to an impedance value range i, on the basis of a frequency distribution of all EIT pixels among the impedance value ranges and on the basis of the lung compliance value C.M.

An inspiration maneuver is triggered for determining the lung compliance value C.M. This should be understood to mean that the lung is influenced in targeted fashion during inspiration. According to the invention, influence can be exerted by means of a ventilator, very particularly preferably by means of a ventilator for pressure support ventilation. The lung compliance value C.M can be determined by virtue of ascertaining a compliance of the entire lung. To this end, an end-expiratory pressure, an end-inspiratory pressure and a tidal volume are preferably measured, the compliance of the entire lung being determined therefrom. The end-expiratory pressure and/or the end-inspiratory pressure are preferably measured during an occlusion of the airways. It is also possible for a surrogate for the compliance of the entire lung to be measured in order to determine the lung compliance value. Here, use can be made of different methods which are suitable for sufficiently accurately determining the lung compliance value.

An end-inspiratory electrical impedance Z.INSP is determined for each EIT pixel and an end-expiratory electrical impedance Z.EXSP is determined for each EIT pixel. This is preferably implemented at the start or at the end of an inspiration process of the lung, during which the above-described inspiration maneuver is also triggered. However, Z.INSP and Z.EXSP could also alternatively be determined during preceding or subsequent respiratory movements. It is advantageous if an electrical impedance is captured continuously for each EIT pixel, from the measurement of the expiratory electrical impedance to the measurement of the end-inspiratory electrical impedance.

The impedance difference $\Delta Z$ for each EIT pixel is determined by virtue of calculating the difference between Z.INSP and Z.EXSP. The respective impedance differences $\Delta Z$ of the EIT pixels are indicators for a state of the lung in different lung regions, which allows conclusions about the regional compliance $C.REG_i$ to be drawn. The EIT pixels are assigned to the impedance value ranges on the basis of their respective value $\Delta Z$. Now, the regional compliance $C.REG_i$ can be determined on the basis of a frequency distribution of all EIT pixels among the impedance value ranges and on the basis of the lung compliance value C.M. What is advantageously exploited here is that there is a relationship between the impedance differences $\Delta Z$ of the EIT pixels and the characteristic of the compliance in different regions of the lung. The regional compliance $C.REG_i$ relates to specific EIT pixels which are assigned to an impedance value range i, where i is an index which distinguishes different impedance value ranges from one another. Consequently, the so-called regional compliance $C.REG_i$ is present in regions of the lung captured by these specific EIT pixels.

Let there be a total of m different impedance value ranges. Then, it is also possible to determine m regional compliances $C.REG_i$ within the lung, with the index i=1, 2, . . . , m. According to the invention, these regional compliances can be collected and output, for example on a display means or in a digital data format. According to the invention, the regional compliances can be ascertained at different times such that a time profile of the regional compliances in different lung regions can be understood.

The regional compliance $C.REG_i$ is preferably determined during a pressure support ventilation of the lung. The expression "pressure support ventilation of the lung" should be understood to mean that the lung function during spontaneous respiration is assisted by the application of additional pressure, which was fixedly predetermined, which orients itself on a target volume or which is realized in proportional fashion with respect to the flow resistances and the inspiratory volume. Thus, spontaneous respiration is assisted. Respiration rate and depth of breathing can usually be determined by the patient themselves. Pressure support ventilation is implemented by means of a ventilator. As a rule, a desired pressure is preset. This form of ventilation can be used for weaning off ventilators, for example.

Preferably, the inspiration maneuver is an end-inspiratory hold maneuver which is carried out during pressure support ventilation of the lung. An end-inspiratory hold maneuver should be understood to mean a ventilation maneuver in which the airflow is interrupted toward the end or at the end of inspiration. According to embodiments of the invention, an end-inspiratory pressure used to determine the lung compliance value C.M can be measured during the end-inspiratory hold maneuver. According to the invention, the end-inspiratory electrical impedance Z.INSP can further be measured during the end-inspiratory hold maneuver. Provision can be made according to the invention for the end-inspiratory hold maneuver to be triggered on the basis of a measured pressure, on the basis of a magnitude of a volumetric flow into the lung, on the basis of a volume supplied to the lung and/or on the basis of any other parameter. A time at which the end-inspiratory maneuver is triggered can also be determined manually. Further information for determining the compliance by means of end-inspiratory hold maneuver can be gathered from the article "End-inspiratory airway occlusion: a method to assess the pressure developed by inspiratory muscles in patients with acute lung injury undergoing pressure support", Foti et al., American Journal of Respiratory and Critical Care Medicine, Volume 156, No. 4 Pt. 1, pp. 1210-1216, 1997 and from the article "Driving Pressure Is Associated with Outcome during Assisted Ventilation in Acute Respiratory Distress Syndrome", Bellani et al., Anesthesiology, Volume 131, No. 3, pp. 594-604, 2019. The entire disclosures of the documents just mentioned are incorporated by reference herein.

According to the invention, provision can be made for the lung compliance value C.M to be determined as per $$C.M = \frac{TV}{P.PLATEAU - EEP}$$

where TV is a tidal volume of the lung, where P.PLATEAU is an end-inspiratory plateau pressure which sets in during the end-inspiratory hold maneuver and where EEP is an end-expiratory pressure. The tidal volume TV denotes a lung volume that is preferably determined during inspiration. By way of example, it can be determined by means of a flow sensor. The end-expiratory pressure is preferably determined before the start of inspiration. The end-inspiratory plateau pressure sets in after a short time under occlusion of the airways following the trigger of the end-inspiratory hold maneuver. As a rule, it is above a peak pressure of spontaneous respiration. Preferably, the end-inspiratory electrical impedance Z.INSP is determined precisely when the end-inspiratory plateau pressure P.PLATEAU has set in.

According to an advantageous embodiment of the invention, the regional compliance $C.REG_i$ is determined as per $$C.REG_i = \frac{W_i \cdot UB}{\sum_{n=1}^{m}(NPX_n * W_n \cdot UB)} * C.M * \sum_{n=1}^{m} NPX_n$$

wherein the EIT pixels are assigned to a plurality of impedance value ranges, of which there are a total of m, where $NPX_n$ is a number of EIT pixels which are assigned to an n-th impedance value range of the m impedance value ranges, where $W_i.UB$ is an upper bound of the impedance value range i and where $W_n.UB$ is an upper bound of the n-th impedance value range of the m impedance value ranges.

A total of m impedance value ranges $W_1, W_2, \ldots, W_m$ is provided. The n-th impedance value range $W_n$ has an upper bound $W_n.UB$. The impedance value range i, which should be denoted $W_i$, where $1 \leq i \leq m$ applies, has an upper bound $W_i.UB$. By means of the formula listed above, the lung compliance value C.M is weighted in respect of the impedance value ranges and the EIT pixels to be assigned thereto such that the regional compliances $C.REG_i$ arise for different impedance value ranges i.

According to the invention, provision can be made for the impedance value ranges to be ascertained by virtue of a minimum ascertained impedance difference $\Delta Z_{min}$ being subtracted from a maximum ascertained impedance difference $\Delta Z_{max}$ and an arising numerical range being subdivided into sections of equal size, with the sections forming the impedance value ranges. The minimum impedance difference $\Delta Z_{min}$ and the maximum impedance difference $\Delta Z_{max}$ are determined in order to ascertain an overall lower bound and an overall upper bound for the impedance value ranges considered. A numerical range arising is subdivided into sections of equal size. However, according to alternative embodiments, it is also possible to subdivide the numerical range into sections of different size such that impedance value ranges of different size arise.

Preferably, an EIT pixel with a difference value of $\Delta Z$ is assigned to an impedance value range $W_n$ with a lower bound $W_n.LB$ and with an upper bound $W_n.UB$ precisely if the following applies:

$$W_n.LB \leq \Delta Z < W_n.UB$$

or $$W_n.LB < \Delta Z \leq W_n.UB.$$

Each impedance value range has a lower bound $W_n.LB$ and an upper bound $W_n.UB$. Different assignment rules can be used.

According to the invention, provision can be made for a portion $A_i$ of a lung volume in which the regional compliance $C.REG_i$ is present to be determined in the method as per $$A_i = \frac{NPX_i}{\sum_{n=1}^{m} NPX_n}$$

wherein the EIT pixels are assigned to m impedance value ranges, where $NPX_i$ is a number of specific EIT pixels and where $NPX_n$ is a number of EIT pixels which are assigned to an n-th impedance value range of the m impedance value ranges. This establishes which portion of the EIT pixels has the regional compliance $C.REG_i$.

According to a further aspect of the invention, a system for determining a regional compliance $C.REG_i$ of a lung during spontaneous respiration is proposed, wherein the system comprises a device for electrical impedance tomography and means for determining a lung compliance value C.M by measuring a compliance of the lung or by measuring a surrogate for the compliance of the lung and wherein the system is set up to carry out the above-described method. Such a system can determine the regional compliance. According to possible embodiments of the invention, this can relate to an independent appliance. In particular, a device for electrical impedance tomography can be embodied as an independent appliance, which can interact and interchange data with a ventilator, for example. To this end, the ventilator and the device for electrical impedance tomography are coupled by means of at least one interface. Accordingly, the ventilator and the device for electrical impedance tomography each have at least one interface.

The means for determining a lung compliance value C.M can then be formed in the ventilator or in the device for electrical impedance tomography.

However, it is also possible for the system to be integrated in a different apparatus and/or be suitable for use together with a different apparatus. The means for determining the compliance preferably comprise a pressure sensor, a flow sensor and/or a respiratory gas source.

Preferably, the system for determining the regional compliance $C.REG_i$ comprises a computer unit and/or a display means. The computer unit is preferably set up to calculate the regional compliance $C.REG_i$ on the basis of output values of the device for electrical impedance tomography, of the pressure sensor and/or of the flow sensor (of the ventilator). According to the invention, the computer unit can further be set up to calculate a portion $A_i$ of a lung volume in which the regional compliance $C.REG_i$ is present. Further, the computer unit can be set up to prompt the display means to output the regional compliance $C.REG_i$ and/or the portion $A_i$. The regional compliance $C.REG_i$ is preferably output in units of ml/mbar. The portion $A_i$ is preferably output as a percentage.

By way of example, the computer unit is embodied as part of the ventilator and set up to carry out the method steps according to the invention and the calculations required to this end. Alternatively, the computer unit is embodied as part of the system or the device for electrical impedance tomography and set up to carry out the method steps according to the invention and the calculations required to this end.

According to the invention, the system can be set up to determine a lung compliance value C.M by triggering an inspiration maneuver and either by measuring a compliance of the entire lung or by measuring a surrogate for the compliance of the entire lung, to capture an electrical impedance distribution along at least one two-dimensional section through a human thorax by means of a device for electrical impedance tomography, to subdivide the captured electrical impedance distribution at different times into a multiplicity of EIT pixels, to determine an end-expiratory electrical impedance Z.EXSP for each EIT pixel and an end-inspiratory electrical impedance Z.INSP for each EIT pixel, to determine an impedance difference $\Delta Z$ for each EIT pixel by virtue of calculating a difference between the end-inspiratory electrical impedance Z.INSP and the end-expiratory electrical impedance Z.EXSP, to provide a plurality of impedance value ranges and to assign the EIT pixels to the impedance value ranges on the basis of the respective impedance difference $\Delta Z$ of the EIT pixels and to determine the regional compliance $C.REG_i$ for specific EIT pixels, which are assigned to an impedance value range i, on the basis of a frequency distribution of all EIT pixels among the impedance value ranges and on the basis of the lung compliance value C.M.

Provision can further be made for the system to be suitable for carrying out the determination of the regional compliance $C.REG_i$ during a pressure support ventilation of the lung. It is further possible that the inspiration maneuver which triggers the system is an end-inspiratory hold maneuver, wherein the system is set up to carry out the end-inspiratory hold maneuver during pressure support ventilation of the lung.

Preferably, the system is set up to determine the lung compliance value C.M as per $$C.M = \frac{TV}{P.PLATEAU - EEP}$$

where TV is a tidal volume of the lung, where P.PLATEAU is an end-inspiratory plateau pressure which sets in after the end-inspiratory hold maneuver has been triggered and where EEP is an end-expiratory pressure.

Particularly preferably, the system is set up to determine the regional compliance $C.REG_i$ as per $$C.REG_i = \frac{W_i \cdot UB}{\sum_{n=1}^{m}(NPX_n * W_n \cdot UB)} * C.M * \sum_{n=1}^{m} NPX_n$$

wherein the EIT pixels are assigned to m impedance value ranges, where $NPX_n$ is a number of EIT pixels which are assigned to an n-th impedance value range of the m impedance value ranges, where $W_i.UB$ is an upper bound of the impedance value range i and where $W_n.UB$ is an upper bound of an n-th impedance value range of the m impedance value ranges.

According to the invention, it is possible for the system to be set up to ascertain the impedance value ranges by virtue of it subtracting a minimum ascertained impedance difference $\Delta Z_{min}$ from a maximum ascertained impedance difference $\Delta Z_{max}$ and subdividing an arising numerical range into sections of equal size, with the sections forming the impedance value ranges. Further, the system can be set up in such a way that it assigns an EIT pixel with the difference value of $\Delta Z$ to an impedance value range $W_n$ with a lower bound $W_n.LB$ and with an upper bound $W_n.UB$ precisely if the following applies:

$$W_n.LB \leq \Delta Z < W_n.UB$$

or $$W_n.LB < \Delta Z \leq W_n.UB.$$

An advantageous embodiment of the system is configured to determine a portion A of a lung volume in which the regional compliance $C.REG_i$ is present as per $$A = \frac{NPX_i}{\sum_{n=1}^{m} NPX_n}$$

wherein the EIT pixels are assigned to m impedance value ranges, where $NPX_i$ is a number of specific EIT pixels and where $NPX_n$ is a number of EIT pixels which are assigned to an n-th impedance value range of the m impedance value ranges.

According to a further aspect of the invention, a ventilator is proposed, the latter comprising the above-described system for determining a regional compliance, wherein the ventilator is suitable for pressure support ventilation, for example. According to the invention, the system for determining the regional compliance can form part of the ventilator and can preferably also be used for functions that go beyond the determination of the regional compliance. By way of example, the ventilator is suitable for pressure support ventilation. Thus, it can assist a lung with spontaneous respiration, for example. As per possible embodiments, this can be implemented by virtue of the ventilator monitoring a respiratory flow and the ventilator applying inspiratory pressure to the airways if the lung does not bring about a sufficient respiratory flow.

According to the invention, provision can be made for the ventilator to be set up to trigger the inspiration maneuver in manual, automatic and/or cyclical fashion. In the case of a manual trigger, the ventilator triggers the inspiration maneuver following an external prompt, for example when a switch is actuated by a user. In this case, determining the regional compliance $C.REG_i$ is prompted by the user. In the case of an automatic trigger, the inspiration maneuver is triggered by the ventilator when a predefined condition is satisfied. By way of example, the predefined condition can be a respiration rate, a respiratory pressure undershot by the user or any other physiological or other type of parameter. In the case of a cyclical trigger, the inspiration maneuver is triggered independently at corresponding temporal intervals by the ventilator.

According to a further aspect of the teaching, the ventilator is set up to adapt a pressure on the basis of at least a regional compliance, the pressure being a positive end-expiratory pressure in particular, to adapt a tidal volume and/or to trigger a recruiting maneuver. The ventilator can further be set up to adapt other treatment parameters. By way of example, this allows therapeutic actions to be automatically triggered by the ventilator. The at least one compliance can be the regional compliance $C.REG_i$ and/or compliances which the ventilator has determined for other lung regions. In many cases, the regional compliance forms an assessment feature which can be used on its own or in combination with other physiological parameters to trigger the above-described actions. The positive end-expiratory pressure is a pressure that the ventilator applies to the airways at the end of expiration in order to avoid a collapse of alveoli. The tidal volume is the tidal air. The ventilator can be set up to ensure a certain minimum tidal air and the latter can be adapted according to the invention on the basis of the regional compliance. Recruiting maneuvers are ventilation maneuvers which serve the purpose of aerating collapsed lung regions and/or preventing a collapse of the lung or of portions of the lung.

It is advantageous if the ventilator comprises a display means and is set up to graphically represent a plurality of regional compliances in different lung areas. According to the invention, the display means can be a screen or the like. According to a special embodiment, the regional compliances are presented graphically on the basis of an image representation of a lung. According to the invention, regions of the lung in which comparatively high regional compliances are present can be represented by a different color or a different brightness than regions of the lung in which comparatively low regional compliances are present. Consequently, an observer can easily understand a local distribution of the regional compliances in the lung.

The invention also relates to a device for electrical impedance tomography, comprising a system or embodied as part of a system, wherein the device for electrical impedance tomography comprises at least one display means, at least one computer unit and means for determining a lung compliance value C.M by measuring a compliance of the lung or by measuring a surrogate for the compliance of the lung.

BRIEF DESCRIPTION OF THE DRAWINGS

Further aspects of the invention are explained in exemplary fashion on the basis of the drawings. In the figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
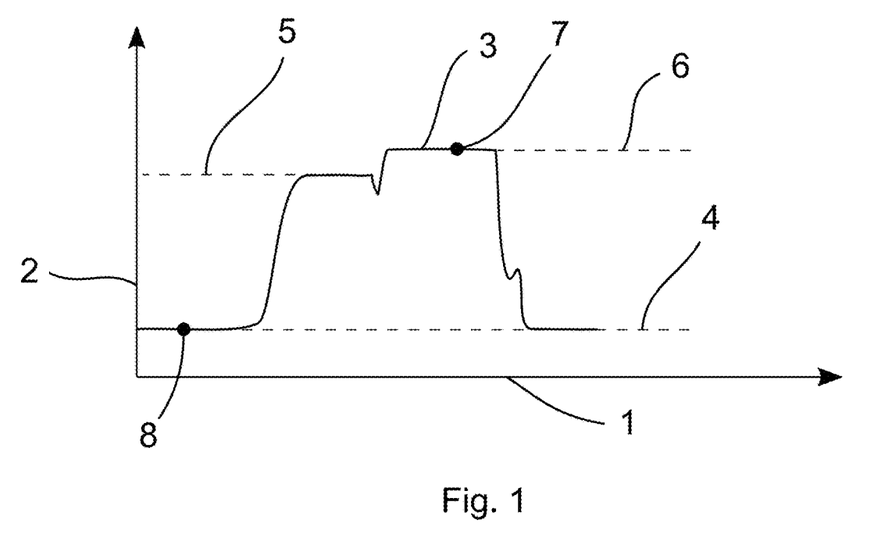
FIG. 1 shows a representation of a pressure profile of an airways pressure during an end-inspiratory hold maneuver and FIG. 2 shows a scatterplot which reproduces a percentage distribution of regional compliances in a lung.

FIG. 1 shows a representation of a pressure profile 3 of an airways pressure during an end-inspiratory hold maneuver. The pressure profile 3 is plotted on a time axis 1 and a pressure axis 2. The illustrated pressure profile shows a typical curve of the pressure change during an end-inspiratory hold maneuver under pressure supported spontaneous respiration. Initially, an end-expiratory pressure 4 is present, the level of which is represented by the lower dashed line. The end-expiratory pressure 4 sets in at the end of expiration. Measurements are preferably carried out when the airways are occluded; to this end, a first measurement point 8 is recorded in exemplary fashion.

During inspiration, the airways pressure increases and there initially is an end-inspiratory pressure 5, the level of which is represented by the upper left-hand, dashed line in the representation as per FIG. 1. Now, an end-inspiratory hold maneuver is triggered, i.e., the airflow is interrupted, for example by means of a ventilator. In this case, an end-inspiratory plateau pressure 6 is set in, the latter being represented by means of the further upper right-hand, dashed line in the representation as per FIG. 1. As a rule, the end-inspiratory plateau pressure 6 lies above the end-inspiratory pressure 5 in the case of pressure support ventilation. Now—while the occlusion of the airways is maintained—the end-inspiratory plateau pressure 6 is measured, here in exemplary fashion at a second measurement point 7. After the occlusion of the airways has been lifted, expiration can take place, with the airways pressure dropping and the end-expiratory pressure 4 setting in again.

Figure 2:
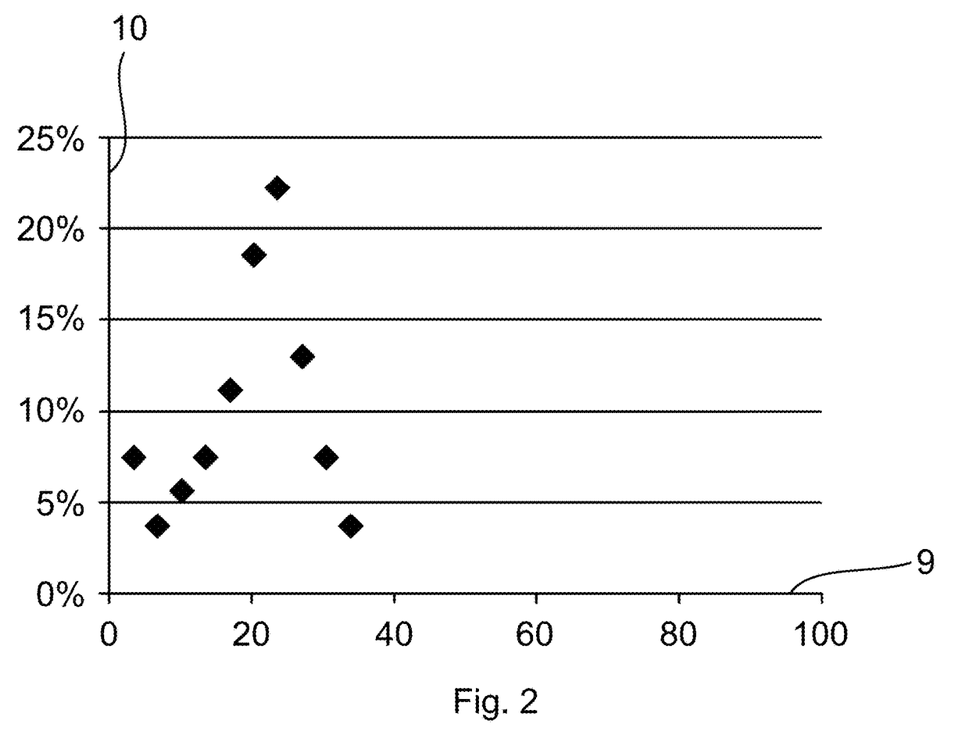

FIG. 2 shows a scatterplot which reproduces a percentage distribution of regional compliances in a lung. A regional compliance in units of ml/mbar is plotted along the X-axis 9. A portion of EIT pixels, to which the respective regional compliance should be assigned, is plotted along the Y-axis 10. Consequently, it is possible to understand the distribution in terms of portion of the regional compliance within the lung. The method for calculating the regional compliances is explained below on the basis of exemplary values, for the purposes of which reference is made in exemplary fashion to the following table 1:

TABLE 1

| Impedance value range i | $W_i \cdot UB$ | $NPX_i$ | $UNW_i$ | $CONTRIB_i$ |
|---|---|---|---|---|
| 1 | 5 | 40 | 0.250 | 10.000 |
| 2 | 10 | 20 | 0.500 | 10.000 |
| 3 | 15 | 30 | 0.750 | 22.500 |
| 4 | 20 | 40 | 1.000 | 40.000 |
| 5 | 25 | 60 | 1.250 | 75.000 |
| 6 | 30 | 100 | 1.500 | 150.000 |
| 7 | 35 | 120 | 1.750 | 210.000 |
| 8 | 40 | 70 | 2.000 | 140.000 |
| 9 | 45 | 40 | 2.250 | 90.000 |
| 10 | 50 | 20 | 2.500 | 50.000 |

This is based on a measurement of an end-expiratory pressure EEP and an end-inspiratory plateau pressure P.PLATEAU. Electrical impedance tomography is used to measure an impedance value Z.EXSP in different lung regions at the time at which the end-expiratory pressure EEP is measured. Electrical impedance tomography is used to measure an electrical impedance Z.INSP in different lung regions at the time at which the end-inspiratory plateau pressure P.PLATEAU is measured. The measured electrical impedances are assigned to different EIT pixels.

An impedance difference $\Delta Z = Z.INSP - Z.EXSP$ is calculated for each EIT pixel from value pairs Z.EXSP and Z.INSP. Table 1 lists impedance value ranges i. The impedance value ranges each have the same size, and so, for example, a lower bound $W_1.LB = 0$ and an upper bound $W_1.UB = 5$ arise for a first impedance value range 1, in this case specified as dimensionless variables. The table specifies upper bounds $W_i.UB$ of the impedance value ranges. In an adjacent column a number of EIT pixels $NPX_i$ are specified for each impedance value range, said EIT pixels being assigned to the respective value range on account of their impedance difference $\Delta Z$. An unweighted intermediate value $UNW_i$ is calculated for each impedance value range. The unweighted intermediate value is determined according to the formula:

$$UNW_i = W_i.UB / (P.PLATEAU - EEP)$$

In the present example, 20 mbar is assumed to be the pressure difference between P.PLATEAU and EEP. A contribution to the compliance is specified in an adjacent column; it is calculated as per the formula:

$$CONTRIB_i = NPX_i * UNW_i$$

The calculation is continued in table 2. A normalized intermediate value for the i-th impedance value range is calculated as per the formula:

$$UNW\_NORM_i = UNW_i * C.M / \sum_{n=1}^{10} CONTRIB_n$$

Here, C.M is a compliance of the entire lung and calculated, for example, as per the formula:

$$C.M = \frac{TV}{P.PLATEAU - EEP}$$

from a measured tidal volume TV, the measured end-inspiratory plateau pressure P.PLATEAU and the measured end-expiratory pressure EEP. In the present case, a compliance C.M=20 ml/mbar is assumed.

TABLE 2

| i | $UNW\_NORM_i$ | $C.REG_i$ [ml/mbar] | $A_i$ |
|---|---|---|---|
| 1 | 0.006 | 3.39 | 7% |
| 2 | 0.012 | 6.77 | 4% |
| 3 | 0.018 | 10.16 | 6% |
| 4 | 0.025 | 13.54 | 7% |
| 5 | 0.031 | 16.93 | 11% |
| 6 | 0.037 | 20.31 | 19% |
| 7 | 0.043 | 23.70 | 22% |
| 8 | 0.050 | 27.08 | 13% |
| 9 | 0.056 | 30.47 | 7% |
| 10 | 0.062 | 33.86 | 4% |

Finally, a regional compliance $C.REG_i$ is calculated as per the formula:

$$C.REG_i = UNW\_NORM_i * NPX_i$$

If this is based on the calculation process described above, it is possible to derive the simplified formula:

$$C.REG_i = \frac{W_i \cdot UB}{\sum_{n=1}^{m}(NPX_n * W_n \cdot UB)} * C.M * \sum_{n=1}^{m} NPX_n$$

therefrom. To determine a portion of the EIT pixels in which the regional compliance $C.REG_i$ can be found, a portion of the lung volume $A_i$ is calculated as per the formula:

$$A_i = \frac{NPX_i}{\sum_{n=1}^{m} NPX_n}$$

The values of $C.REG_i$ and $A_i$ ascertained above are presented in FIG. 2 in visualized fashion. From such a visualization, it is possible to draw conclusions about the state of the lung and, where necessary, it is possible to introduce therapeutic measures or adapt ventilation parameters.

To sum up, the present invention provides:

1. A method for determining a regional compliance $C.REG_i$ of a lung, wherein the method comprises:
    capturing an electrical impedance distribution along at least one two-dimensional section through a human thorax by a device for electrical impedance tomography (EIT),
    triggering a ventilation maneuver and determining the electrical impedance distribution from a start of inspiration to an end of expiration and measuring a compliance of the entire lung or measuring a surrogate for the compliance of the entire lung,
    wherein the compliance corresponds to the highest impedance (pixel density) of the EIT,
    determining the regional compliance by dividing an ascertained impedance among a number of lung regions and assigning the impedance to the lung regions.

2. A method for determining a regional compliance $C.REG_i$ of a lung during spontaneous respiration, wherein the method comprises:
    determining a lung compliance value C.M by triggering an inspiration maneuver and either measuring a compliance of the entire lung or measuring a surrogate for the compliance of the entire lung,
    capturing an electrical impedance distribution along at least one two-dimensional section through a human thorax by a device for electrical impedance tomography,
    dividing a captured electrical impedance distribution at different times into a multiplicity of EIT pixels,
    determining an end-expiratory electrical impedance Z.EXSP for each EIT pixel and an end-inspiratory electrical impedance Z.INSP for each EIT pixel,
    determining an impedance difference $\Delta Z$ for each EIT pixel by virtue of calculating a difference between the end-inspiratory electrical impedance Z.INSP and the end-expiratory electrical impedance Z.EXSP,
    providing a plurality of impedance value ranges and assigning the EIT pixels to the impedance value ranges based on a respective impedance difference $\Delta Z$ of the EIT pixels,
    determining the regional compliance $C.REG_i$ for specific EIT pixels, which are assigned to an impedance value range i, on the basis of a frequency distribution of all EIT pixels among the impedance value ranges and on the basis of the lung compliance value C.M.

3. The method of item 1 or item 2, wherein the regional compliance $C.REG_i$ is determined during pressure support ventilation of the lung.

4. The method of any one of the preceding items, wherein the inspiration maneuver is an end-inspiratory hold maneuver which is carried out during pressure support ventilation of the lung.

5. The method of any one of the preceding items, wherein the lung compliance value C.M is determined as per $$C.M = \frac{TV}{P.PLATEAU - EEP}$$

where TV is a tidal volume of the lung, where P.PLATEAU is an end-inspiratory plateau pressure which sets in during the end-inspiratory hold maneuver and where EEP is an end-expiratory pressure.

6. The method of any one of the preceding items, wherein the regional compliance $C.REG_i$ is determined as per $$C.REG_i = \frac{W_i \cdot UB}{\sum_{n=1}^{m}(NPX_n * W_n \cdot UB)} * C.M * \sum_{n=1}^{m} NPX_n$$

wherein the EIT pixels are assigned to m impedance value ranges, where $NPX_n$ is a number of EIT pixels which are assigned to an n-th impedance value range of the m impedance value ranges, where $W_i.UB$ is an upper bound of the impedance value range i and where $W_n.UB$ is an upper bound of the n-th impedance value range of the m impedance value ranges.

7. The method of any one of the preceding items, wherein the impedance value ranges are ascertained by virtue of a minimum ascertained impedance difference $\Delta Z_{min}$ being subtracted from a maximum ascertained impedance difference $\Delta Z_{max}$ and a resulting numerical range being subdivided into sections of equal size, with the sections forming the impedance value ranges.

8. The method of any one of the preceding items, wherein an EIT pixel with the difference value $\Delta Z$ is assigned to an impedance value range $W_n$ with a lower bound $W_n.LB$ and with an upper bound $W_n.UB$ precisely if the following applies: $W_n.LB \leq \Delta Z < W_n.UB$ or $W_n.LB < \Delta Z \leq W_n.UB$.

9. The method of any one of the preceding items, wherein a portion $A_i$, of a lung volume in which the regional compliance $C.REG_i$ is present is determined as per $$A_i = \frac{NPX_i}{\sum_{n=1}^{m} NPX_n}$$

wherein the EIT pixels are assigned to m impedance value ranges, where $NPX_i$ is a number of specific EIT pixels and where $NPX_n$ is a number of EIT pixels which are assigned to an n-th impedance value range of the m impedance value ranges.

10. A system for determining a regional compliance $C.REG_i$ of a lung during spontaneous respiration and/or during ventilation, wherein the system comprises a device for electrical impedance tomography and elements for determining a lung compliance value C.M by measuring a compliance of the lung or by measuring a surrogate for the compliance of the lung and wherein the system is configured to carry out the method of any one of items 1 to 9.

11. The system of item 10, wherein the system comprises a device for electrical impedance tomography, a ventilator, at least one display element, at least one computer unit and elements for determining a lung compliance value C.M by measuring a compliance of the lung or by measuring a surrogate for the compliance of the lung.

12. The system of any one of item 10 or item 11, wherein the system is configured to determine a lung compliance value C.M by triggering an inspiration maneuver and either by measuring a compliance of the entire lung or by measuring a surrogate for the compliance of the entire lung, to capture an electrical impedance distribution along at least one two-dimensional section through a human thorax by a device for electrical impedance tomography, to subdivide the captured electrical impedance distribution at different times into a multiplicity of EIT pixels, to determine an end-expiratory electrical impedance Z.EXSP for each EIT pixel and an end-inspiratory electrical impedance Z.INSP for each EIT pixel, to determine an impedance difference $\Delta Z$ for each EIT pixel by virtue of calculating a difference between the end-inspiratory electrical impedance Z.INSP and the end-expiratory electrical impedance Z.EXSP, to provide a plurality of impedance value ranges and to assign the EIT pixels to the impedance value ranges on the basis of the respective impedance difference $\Delta Z$ of the EIT pixels and to determine the regional compliance $C.REG_i$ for specific EIT pixels, which are assigned to an impedance value range i, on the basis of a frequency distribution of all EIT pixels among the impedance value ranges and on the basis of the lung compliance value C.M.

13. The system of any one of items 10 to 12, wherein the system is configured to determine the lung compliance value C.M as per $$C.M = \frac{TV}{P.PLATEAU - EEP}$$

where TV is a tidal volume of the lung, where P.PLATEAU is an end-inspiratory plateau pressure which sets in after an end-inspiratory hold maneuver has been triggered and where EEP is an end-expiratory pressure.

14. The system of any one of items 10 to 13, wherein the system is configured to determine the regional compliance $C.REG_i$ as per $$C.REG_i = \frac{W_i \cdot UB}{\sum_{n=1}^{m}(NPX_n * W_n \cdot UB)} * C.M * \sum_{n=1}^{m} NPX_n$$

where the EIT pixels are assigned to the m impedance value ranges, where $NPX_n$ is a number of EIT pixels which are assigned to an n-th impedance value range of the m impedance value ranges, where $W_n.UB$ is an upper bound of the impedance value range i and where $W_n.UB$ is an upper bound of an n-th impedance value range of the m impedance value ranges.

15. A ventilator, wherein the ventilator comprises a system according to item 10 or is embodied as part of a system according to item 10, and wherein the ventilator is suitable for pressure support ventilation.

16. The ventilator of item 15, wherein the ventilator is configured to trigger the inspiration maneuver in manual, automatic and/or cyclical fashion.

17. The ventilator of any one of item 15 or item 16, wherein the ventilator is configured to adapt a pressure on the basis of at least a regional compliance, the pressure being a positive end-expiratory pressure in particular, to adapt a tidal volume and/or to trigger a recruiting maneuver.

18. The ventilator of any one of items 15 to 17, wherein the ventilator comprises a display element and is configured to graphically represent a plurality of regional compliances in different lung areas.

19. The ventilator of item 18, wherein a graphical representation of the lung is presented on the display element and at least two regional compliances, in graphically different representation, are presented in the graphical representation of the lung.

20. The ventilator of item 19, wherein the at least two regional compliances are presented on the display element as percentage values or in ml/mbar.

21. A device for electrical impedance tomography, wherein the device comprises a system according to item 10 or is embodied as part of a system according to item 10, and wherein the device further comprises at least one display element, at least one computer unit and elements for determining a lung compliance value C.M by measuring a compliance of the lung or by measuring a surrogate for the compliance of the lung.

LIST OF REFERENCE NUMERALS

1 Time axis
2 Pressure axis
3 Pressure profile
4 End-expiratory pressure
5 End-inspiratory pressure
6 End-inspiratory plateau pressure
7 Second measurement point
8 First measurement point
9 X-axis
10 Y-axis

What is claimed is:

1. A method for determining a regional compliance $C.REG_i$ of a lung, wherein the method comprises:
capturing an electrical impedance distribution along at least one two-dimensional section through a human thorax by a device for electrical impedance tomography (EIT),
triggering a ventilation maneuver and determining the electrical impedance distribution from a start of inspiration to an end of expiration and measuring a compliance of the entire lung or measuring a surrogate for the compliance of the entire lung,
wherein the compliance corresponds to the highest impedance (pixel density) of the EIT, and determining the regional compliance by dividing an ascertained impedance among a number of lung regions and assigning the impedance to the lung regions;

or comprises, in case of determining a regional compliance C.REG; of a lung during spontaneous respiration:

determining a lung compliance value C.M by triggering an inspiration maneuver and either measuring a compliance of the entire lung or a surrogate for the compliance of the entire lung, capturing an electrical impedance distribution along at least one two-dimensional section through a human thorax by a device for electrical impedance tomography, dividing a captured electrical impedance distribution at different times into a multiplicity of EIT pixels, determining an end-expiratory electrical impedance Z.EXSP for each EIT pixel and an end-inspiratory electrical impedance Z.INSP for each EIT pixel, determining an impedance difference $\Delta Z$ for each EIT pixel by virtue of calculating a difference between Z.INSP and Z.EXSP, providing a plurality of impedance value ranges and assigning the EIT pixels to the impedance value ranges based on a respective impedance difference $\Delta Z$ of the EIT pixels, determining the regional compliance $C.REG_i$ for specific EIT pixels, which are assigned to an impedance value range i, based on a frequency distribution of all EIT pixels among the impedance value ranges and based on the lung compliance value C.M, and wherein the regional compliance $C.REG_i$ is determined as per $$C.REG_i = \frac{W_i \cdot UB}{\sum_{n=1}^{m}(NPX_n * W_n \cdot UB)} * C.M * \sum_{n=1}^{m} NPX_n$$

wherein the EIT pixels are assigned to m impedance value ranges, $NPX_n$ is a number of EIT pixels which are assigned to an n-th impedance value range of the m impedance value ranges, $W_i.UB$ is an upper bound of the impedance value range i and $W_n.UB$ is an upper bound of the n-th impedance value range of the m impedance value ranges.

2. The method of claim 1, wherein the regional compliance $C.REG_i$ is determined during pressure support ventilation of the lung.

3. The method of claim 1, wherein the inspiration maneuver is an end-inspiratory hold maneuver which is carried out during pressure support ventilation of the lung.

4. The method of claim 1, wherein the impedance value ranges are ascertained by subtracting a minimum ascertained impedance difference $\Delta Z_{min}$ from a maximum ascertained impedance difference $\Delta Z_{max}$ and subdividing a resulting numerical range into sections of equal size, with the sections forming the impedance value ranges and/or wherein an EIT pixel with the difference value $\Delta Z$ is assigned to an impedance value range $W_n$ with a lower bound $W_n.LB$ and with an upper bound $W_n.UB$ precisely if the following applies:

$W_n.LB \leq \Delta Z < W_n.UB$ or $W_n.LB < \Delta Z \leq W_n.UB$.

5. The method of claim 1, wherein a portion $A_i$ of a lung volume in which the regional compliance $C.REG_i$ is present is determined as per $$A_i = \frac{NPX_i}{\sum_{n=1}^{m} NPX_n}$$

wherein the EIT pixels are assigned to m impedance value ranges, $NPX_i$ is a number of specific EIT pixels and $NPX_n$ is a number of EIT pixels which are assigned to an n-th impedance value range of the m impedance value ranges.

6. A system for determining a regional compliance $C.REG_i$ of a lung during spontaneous respiration and/or during ventilation, wherein the system comprises a device for electrical impedance tomography and elements for determining a lung compliance value C.M by measuring a compliance of the lung or a surrogate for the compliance of the lung and wherein the system is configured to carry out the method of claim 1.

7. The system of claim 6, wherein the system further comprises a ventilator, at least one display element, and at least one computer unit.

8. The system of claim 7, wherein the ventilator (i) is suitable for pressure support ventilation and/or (ii) is configured to trigger the inspiration maneuver in manual, automatic and/or cyclical fashion and/or (iii) is configured to adapt a pressure on the basis of at least a regional compliance to adapt a tidal volume and/or to trigger a recruiting maneuver and/or (iv) comprises a display element and is configured to graphically represent a plurality of regional compliances in different lung areas.

9. The system of claim 6, wherein the system is configured to determine a lung compliance value C.M by triggering an inspiration maneuver and either by measuring a compliance of the entire lung or by measuring a surrogate for the compliance of the entire lung, to capture an electrical impedance distribution along at least one two-dimensional section through a human thorax by a device for electrical impedance tomography, to subdivide the captured electrical impedance distribution at different times into a multiplicity of EIT pixels, to determine an end-expiratory electrical impedance Z.EXSP for each EIT pixel and an end-inspiratory electrical impedance Z.INSP for each EIT pixel, to determine an impedance difference $\Delta Z$ for each EIT pixel by calculating a difference between Z.INSP and Z.EXSP, to provide a plurality of impedance value ranges and to assign the EIT pixels to the impedance value ranges on the basis of the respective impedance difference $\Delta Z$ of the EIT pixels and to determine the regional compliance $C.REG_i$ for specific EIT pixels, which are assigned to an impedance value range i, based on a frequency distribution of all EIT pixels among the impedance value ranges and on the lung compliance value C.M.

10. The method of claim 1, wherein the lung compliance value C.M is determined as per $$C.M = \frac{TV}{P.PLATEAU - EEP}$$

where TV is a tidal volume of the lung, P.PLATEAU is an end-inspiratory plateau pressure which sets in during an end-inspiratory hold maneuver, and EEP is an end-expiratory pressure.

11. The system of claim 8, wherein a graphical representation of the lung is presented on the display element and at least two regional compliances, in graphically different representation, are presented in the graphical representation of the lung.

12. The ventilator of claim 11, wherein the at least two regional compliances are presented on the display element as percentage values or in ml/mbar.

13. A method for determining a regional compliance $C.REG_i$ of a lung during spontaneous respiration, wherein the method comprises:
   determining a lung compliance value C.M by triggering an inspiration maneuver and either measuring a compliance of the entire lung or a surrogate for the compliance of the entire lung,
   capturing an electrical impedance distribution along at least one two-dimensional section through a human thorax by a device for electrical impedance tomography,
   dividing a captured electrical impedance distribution at different times into a multiplicity of EIT pixels,
   determining an end-expiratory electrical impedance Z.EXSP for each EIT pixel and an end-inspiratory electrical impedance Z.INSP for each EIT pixel,
   determining an impedance difference ΔZ for each EIT pixel by virtue of calculating a difference between Z.INSP and Z.EXSP,
   providing a plurality of impedance value ranges and assigning the EIT pixels to the impedance value ranges based on a respective impedance difference ΔZ of the EIT pixels,
   determining the regional compliance $C.REG_i$ for specific EIT pixels, which are assigned to an impedance value range i, based on a frequency distribution of all EIT pixels among the impedance value ranges and based on the lung compliance value C.M.

14. The method of claim 13, wherein the regional compliance $C.REG_i$ is determined during pressure support ventilation of the lung.

15. The method of claim 13, wherein the inspiration maneuver is an end-inspiratory hold maneuver which is carried out during pressure support ventilation of the lung.

16. The method of claim 13, wherein a portion $A_i$ of a lung volume in which the regional compliance $C.REG_i$ is present is determined as per $$A_i = \frac{NPX_i}{\sum_{n=1}^{m} NPX_n}$$

wherein the EIT pixels are assigned to m impedance value ranges, $NPX_i$ is a number of specific EIT pixels and $NPX_n$ is a number of EIT pixels which are assigned to an n-th impedance value range of the m impedance value ranges.

17. A system for determining a regional compliance $C.REG_i$ of a lung during spontaneous respiration and/or during ventilation, wherein the system comprises a device for electrical impedance tomography and elements for determining a lung compliance value C.M by measuring a compliance of the lung or a surrogate for the compliance of the lung and wherein the system is configured to carry out the method of claim 13.

18. The system of claim 17, wherein the system further comprises a ventilator, at least one display element, and at least one computer.

19. The system of claim 17, wherein the system is configured to determine the lung compliance value C.M as per $$C.M = \frac{TV}{P.PLATEAU - EEP}$$

where TV is a tidal volume of the lung, P.PLATEAU is an end-inspiratory plateau pressure which sets in after an end-inspiratory hold maneuver has been triggered and EEP is an end-expiratory pressure.

20. The system of claim 18, wherein the ventilator (i) is suitable for pressure support ventilation and/or (ii) is configured to trigger the inspiration maneuver in manual, automatic and/or cyclical fashion and/or (iii) is configured to adapt a pressure on the basis of at least a regional compliance to adapt a tidal volume and/or to trigger a recruiting maneuver and/or (iv) comprises a display element and is configured to graphically represent a plurality of regional compliances in different lung areas.

* * * * *